United States Patent [19]

Stumpp et al.

[11] Patent Number: 5,072,049

[45] Date of Patent: Dec. 10, 1991

[54] PROCESS FOR THE PREPARATION OF BIS(4-HYDROXYPHENYL) SULFONE

[75] Inventors: Michael Stumpp, Deidesheim; Peter Neumann, Mannheim; Bernd Hupfeld, Speyer; Helmut Reichelt, Neustadt, all of Fed. Rep. of Germany

[73] Assignee: BASF Aktiengesellschaft, Ludwigshafen, Fed. Rep. of Germany

[21] Appl. No.: 460,648

[22] Filed: Jan. 3, 1990

[30] Foreign Application Priority Data

Feb. 1, 1989 [DE]  Fed. Rep. of Germany ........ 3902897
Jul. 24, 1989 [DE]  Fed. Rep. of Germany ........ 3924395

[51] Int. Cl.$^5$ ............................................ C07C 315/04
[52] U.S. Cl. ..................................................... 568/33
[58] Field of Search .......................................... 568/33

[56] References Cited

U.S. PATENT DOCUMENTS

| | | | |
|---|---|---|---|
| 3,297,766 | 1/1967 | Bradley et al. | 568/33 |
| 4,125,562 | 11/1978 | Darragh et al. | 568/33 |
| 4,162,270 | 7/1979 | Ogata et al. | 568/33 |
| 4,778,932 | 10/1988 | Manami et al. | 568/33 |

FOREIGN PATENT DOCUMENTS

| | | |
|---|---|---|
| 220004 | 4/1987 | European Pat. Off. . |
| 0293037 | 11/1988 | European Pat. Off. . |
| 1618023 | 8/1971 | Fed. Rep. of Germany . |
| 2708388 | 8/1978 | Fed. Rep. of Germany . |
| 2804080 | 8/1978 | Fed. Rep. of Germany . |
| 1148975 | 4/1969 | United Kingdom ............... 568/33 |

OTHER PUBLICATIONS

Patent Abstracts of Japan, Abstracts of JP 57-35559, published Feb. 1982 and JP 61-36253 published Feb. 1986.
Derwent Abstract of Japanese Patent 50-106,938, published Aug. 1975 (Seitetsu).
Derwent Abstract of Japanese Patent 57-77,664, published May 1982 (Tokai).

*Primary Examiner*—Mary E. Ceperley
*Attorney, Agent, or Firm*—John H. Shurtleff

[57] ABSTRACT

A process for the preparation of bis(4-hydroxyphenyl) sulfone by reacting phenol with sulfuric acid at a temperature of from 140° to 230° C., wherein the sulfuric acid is metered in to the phenol only after the reaction temperature has been reached, the phenol and sulfuric acid are used in a molar ratio of from 1:1 to 25:1 and the reaction is carried out in the absence of an inert solvent.

8 Claims, No Drawings

PROCESS FOR THE PREPARATION OF BIS(4-HYDROXYPHENYL) SULFONE

The present invention relates to a process for the preparation of bis(4-hydroxyphenyl) sulfone by reacting phenol with sulfuric acid in the absence of an inert solvent.

Bis(4-hydroxyphenyl) sulfone is commercially highly interesting for use in the manufacture of fibers, resins and high temperature-resistant plastics (e.g. polyethersulfones). As the properties of the polymers produced from the bis(4-hydroxyphenyl) sulfone are greatly dependent on the purity of the monomer, there is a need for selective methods of synthesizing bis(4-hydroxylphenyl) sulfone.

DE-A 2,708,388 and EP-A 220,004 disclose processes in which bis(4-hydroxyphenyl) sulfone is produced by reacting phenol with sulfuric acid in the presence of an inert solvent at a temperature of from 150° to 220° C. The yield and purity of the bis(4-hydroxyphenyl) sulfone are improved by continuously removing the solvent from the system by distillation or by distilling off the solvent when the reaction is substantially complete. It is important to effect distillation within the temperature range 160°-200° C. to ensure that the 2,4′-isomer will be isomerized to bis(4-hydroxyphenyl) sulfone.

It is an object of the present invention to provide an improved process for the preparation of bis(4-hydroxyphenyl) sulfone from phenol and sulfuric acid.

Accordingly, we have found an improved process for the preparation of bis(4-hydroxyhenyl) sulfone by the reaction of phenol with sulfuric acid at a temperature of from 140° to 230° C., wherein phenol and sulfuric acid are used in a molar ratio of from 1:1 to 25:1, in the absence of an inert solvent.

Sulfonation reactions (A) are, like sulfone formation (B), reversible equilibrium reactions. A state of thermodynamic equilibrium (C) exists between the two isomers bis(4-hydroxyphenyl) sulfone and 2-hydroxy-4-hydroxyphenyl sulfone. This is shown by the following equations:

medium. However, this procedure has no influence on the distribution of the isomers. As disclosed by DE-A 2,708,388, the thermodynamic equilibrium between the two isomers is advantageously controlled by incorporating a non-system solvent capable of dissolving the undesirable isomer more readily than the desired bis(4-hydroxylphenyl) sulfone and distilling off said solvent at a temperature of from 160° to 200° C. either during the reaction or when the reaction is substantially complete.

We have now found a process for the preparation of bis(4-hydroxyphenyl) sulfone by the reaction of phenol with sulfuric acid at a temperature of from 140° to 230° C., wherein phenol and sulfuric acid are used in a molar ratio of from 1:1 to 25:1 and the reaction is carried out in the absence of an inert solvent.

The process of the invention can be carried out in the manner described below.

The components sulfuric acid and phenol can be together placed in a reaction vessel and heated to the reaction temperature of from 140° to 230° C. It is advantageous, however, to meter the sulfuric acid to the phenol, either continuously or portionwise, during the reaction, preferably starting after the reaction temperature has been reached. The co-use of a Lewis acid such as boric acid or trifluoromethane sulfonic acid is recommended.

The molar ratio of phenol to sulfuric acid is from 1:1 to 25:1, preferably from 2.1:1 to 10:1 and more preferably from 3:1 to 7:1. Larger amounts are also possible.

The process of the invention may be carried out batchwise in stirred vessels. Continuous operation of the process of the invention may be advantageously effected in reactors comprising one or more tubes. The residence time of the solution in such a tubular reactor may be controlled, for example by filling the reactor with packing elements. We prefer to use spherical packing elements such as are employed in packed columns for fractional distillation of mixtures, for example glass balls or steel balls inert to the reaction mixture. The diameter of such balls is usually from 0.4 to 10 mm, preferably from 1 to 5 mm. It is advantageous to use

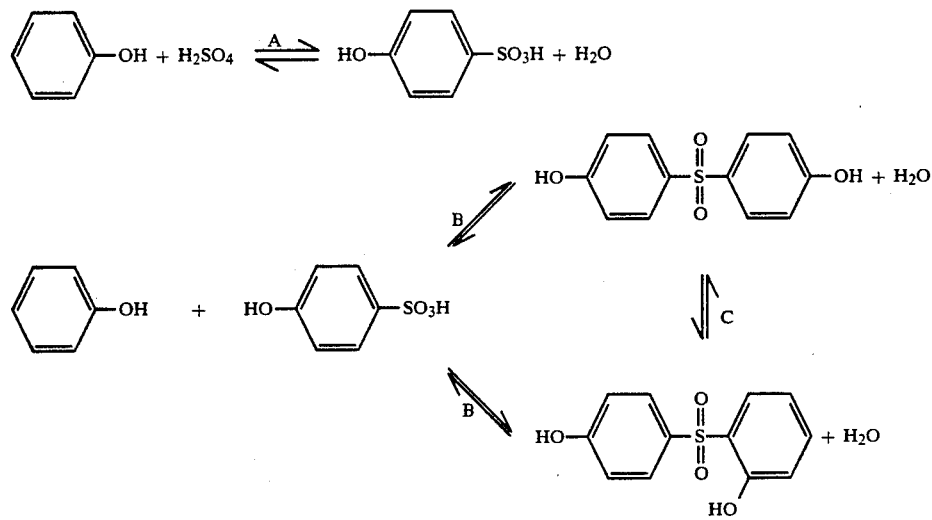

As is well known, the position of equilibrium of both sulfonation (A) and sulfone formation (B) can be influenced almost entirely in favor of the forward reaction by removing the water of reaction from the reaction balls of a specific size. The reaction tubes may be filled with packing elements of a material which has a catalytic effect on sulfone formation, so that such elements are also effective as sulfonating catalysts. For example, the yield and the selective effect of the reaction may be improved by using packing elements comprising boric acid balls inert to gas or silica gel elements doped with an acid such as phosphoric, sulfuric or boric acid. Such modified silica gel is advantageously prepared by impregnating silica gel with an aqueous solution of the acid concerned followed by drying.

It is an advantage of the process of the invention that it is not absolutely necessary to remove the water of reaction from the system in order to achieve complete conversion of the sulfuric acid.

The reaction is generally carried out at a temperature of from 140° to 230° C., preferably from 160° to 200° C. and more preferably from 170° to 190° C. Below 165° C. it is advantageous to use reduced pressure to ensure boiling of the phenol. Usually, however, the process will be run at atmospheric pressure.

Alternatively, the water formed during sulfonation of phenol with sulfuric acid may, according to the invention, be continuously removed from the system by azeotropic distillation by means of the excess phenol present in the reaction mixture, the phenol being recycled to the reactor after phase separation from the water. When, as a rule, at least 50%, but preferably from 80–100% of the theoretical amount of water of reaction has been removed, the phenol is generally no longer recycled to the reaction but is gradually distilled off at from 160° to 200° C.

The reaction time in the batchwise mode is generally from 4 to 6 hours and the time required for isomerization is from 1 to 4 hours. In the continuous mode, i.e. when the reactants pass through a tubular reactor, up to 60% conversion of the sulfuric acid is achieved with residence times between 1 and 3 minutes. By continuously recycling the effluent reaction mixture to the packed column serving as reactor to increase the average residence time to about 15 minutes, it is possible to enhance conversion of the sulfuric acid to 95%.

For purification purposes, the crude product may be taken up in aqueous alkali solution and treated, if necessary, with active carbon followed by filtration and then reprecipitated with an acid, for example a mineral acid, particularly sulfuric acid, at a pH of from about 6 to 7.

EXAMPLES

Example 1

470.6 g (5.0 moles) of phenol, 102.2 g (1.0 mole) of 96% sulfuric acid and 6.2 g (0.1 mole) of boric acid were placed in a glass flask having a capacity of 2 liters and the mixture was heated to 180°–186° C. This temperature was maintained and water removed from the system with recycling of phenol until no more water of reaction was formed. The excess phenol was then distilled off over a period of 2 hours, the temperature not falling below 160° C. [GC analysis of the crude mixture gave the following composition: 5% phenol, 3% isomeric sulfone and 92% bis(4-hydroxyphenyl) sulfone]. To remove the residual traces of phenol, the residue was dissolved in 10% w/w aqueous sodium hydroxide solution and the bis(4-hydroxyphenyl) sulfone precipitated by acidification with sulfuric acid. The precipitate was filtered off in vacuo and dried to give 212 g (0.85 mole; 85% yield) of bis(4- hydroxyphenyl) sulfone showing a purity of >98%.

Example 2

470.6 g (5.0 moles) of phenol and 6.2 g (0.1 mole) of boric acid were placed in a glass flask having a capacity of 2 liters. While the mixture was heated to 180°–186° C., 102.2 g (1.0 mole) of 96% sulfuric acid were added dropwise, after which the water of reaction was removed at 180°–186° C. The phenol was then distilled off over a period of 2 hours at a temperature of from 160° to 200° C. Analysis of the crude product revealed the following composition: 3% phenol, 1% isomeric sulfone and 97% bis(4-hydroxyphenyl) sulfone. Further purification was conducted as described in Example 1. There were obtained 205 g (0.82 mole; yield 82%) of bis(4-hydroxylphenyl) sulfone showing a purity of >99%.

Example 3

102 g (1.0 mole) of 96% sulfuric acid and 546 g (6.0 moles) of phenol were simultaneously fed dropwise over a period of 30 minutes to a vertical glass tube (length 80 cm, diameter 4 cm) heated at 180° C. and packed with glass balls (diameter 4 mm). The residence time of the reaction mixture in the packed column was about 1 to 3 minutes. The effluent reaction mixture was collected and excess phenol was distilled off. The residue was dissolved in 5–10% sodium hydroxide solution and bis(4-hydroxyphenyl) sulfone was then precipitated therefrom by the addition of sulfuric acid to a pH of from 6.5 to 7.0. After filtration and drying, there were obtained 145 g (58%) of bis(4-hydroxyphenyl) sulfone 98.5% pure.

Example 4

Example 3 was repeated except that the effluent reaction mixture was continuously recycled to the packed reactor at a pump rate of 2 liters/h over a period of 2 to 3 hours. The crude product was worked up as described in Example 3 to give 202.5 (81%) of bis(4-hydroxyphenyl) sulfone showing a purity of 98.7%.

Example 5

Example 4 was repeated except that the reaction was carried out at 60° C. under a pressure of from 700 to 900 mbar. After purification there were obtained 197.5 g (79%) of bis(4-hydroxyphenyl) sulfone of 98.3% purity.

Example 6

Example 4 was repeated except that the reactor was packed with sintered boric acid balls (diameter 3 to 5 mm) instead of glass balls. After purification, there were obtained 235 g (94%) of bis(4-hydroxyphenyl) sulfone showing a purity of 99.2%.

Example 7

Example 5 was repeated except that the reactor was packed with sintered boric acid balls instead of glass balls. After purification, there were obtained 227.5 (91%) of bis(4-hydroxyphenyl) sulfone of 99.0% purity.

We claim:

1. In a process for the preparation of bis(4-hydroxyphenyl) sulfone by reacting phenol with sulfuric acid at a temperature of from 140° to 230° C., the improvement which comprises:

metering in the sulfuric acid to the phenol only after heating up to the reaction temperature, using the phenol and sulfuric acid in a molar ratio of from 1:1 to 25:1, and carrying out the reaction in the absence of an inert solvent.

2. A process as claimed in claim 1, wherein the reaction is carried out at a temperature of from 160° to 200° C.

3. A process as claimed in claim 1, wherein the reaction is carried out in excess phenol in the absence of an inert solvent and the excess phenol is gradually distilled off at from 160° to 200° C. during and after the initial stage of the reaction or during and after the intermediate stage of the reaction or the phenol is removed by distillation when the reaction is substantially complete.

4. A process as claimed in claim 1, wherein the phenol and sulfuric acid are used in a molar ratio of from 2.1:1 to 25:1.

5. A process as claimed in claim 1, wherein the reaction is carried out under a pressure of from 0.5 to 1.5 bar.

6. A process as claimed in claim 1, wherein the reaction is carried out in the presence of a sulfonating catalyst.

7. A process as claimed in claim 1, wherein the phenol to sulfuric acid molar ratio is from 3:1 to 7:1.

8. A process as claimed in claim 6, wherein the sulfonating catalyst is boric acid.

* * * * *